(12) United States Patent
Wang et al.

(10) Patent No.: US 11,471,309 B2
(45) Date of Patent: Oct. 18, 2022

(54) INTRAVASCULAR STENT, PREPARATION METHOD AND USE THEREOF

(71) Applicant: SUZHOU VENMED TECHNOLOGY CO., LTD., Jiangsu (CN)

(72) Inventors: Xiaotian Wang, Jiangsu (CN); Haiquan Feng, Jiangsu (CN); Xiaoqiang Li, Jiangsu (CN); Yonggang Wang, Jiangsu (CN)

(73) Assignee: SUZHOU VENMED TECHNOLOGY CO., LTD., Suzhou (CN)

( * ) Notice: Subject to any disclaimer, the term of this patent is extended or adjusted under 35 U.S.C. 154(b) by 128 days.

(21) Appl. No.: 16/878,320

(22) Filed: May 19, 2020

(65) Prior Publication Data

US 2020/0276035 A1    Sep. 3, 2020

Related U.S. Application Data

(63) Continuation-in-part of application No. 15/737,365, filed as application No. PCT/CN2016/089590 on Jul. 11, 2016, now Pat. No. 10,695,201.

(30) Foreign Application Priority Data

Apr. 27, 2016  (CN) .......................... 201610267898.8
Apr. 27, 2016  (CN) .......................... 201610268333.1
(Continued)

(51) Int. Cl.
*A61F 2/915*  (2013.01)
*A61F 2/90*  (2013.01)
(Continued)

(52) U.S. Cl.
CPC .................. *A61F 2/90* (2013.01); *A61F 2/06* (2013.01); *A61F 2/915* (2013.01);
(Continued)

(58) Field of Classification Search
CPC ...... A61F 2002/91525; A61F 2002/821; A61F 2/915–2002/91575; A61F 2250/0037–0039
See application file for complete search history.

(56) References Cited

U.S. PATENT DOCUMENTS 6,190,403 B1    2/2001    Fischell et al.
7,060,088 B1    6/2006    Fischell et al.
(Continued)

FOREIGN PATENT DOCUMENTS

CN      1633264     6/2005
CN      2710576     7/2005
(Continued)

OTHER PUBLICATIONS

International search report dated Dec. 28, 2016 from corresponding application No. PCT/CN2016/089590.

*Primary Examiner* — Rebecca S Preston
(74) *Attorney, Agent, or Firm* — Hauptman Ham, LLP

(57) ABSTRACT

The present disclosure relates to an intravascular stent, preparation method and use thereof, and the intravascular stent comprises a positioning segment and a supporting segment, the positioning segment comprising a plurality of first repeating elements, the supporting segment comprising at least two supporting units and at least one connecting unit, the supporting unit comprising a plurality of second repeating elements, the number of the first repeating elements differing from the number of the second repeating elements, a plane formed by front ends of the plurality of first repeating elements being vertical to or intersecting with the axis of the intravascular stent. The intravascular stent of the present disclosure is particularly suitable for iliac vein, with good supporting effect for iliac vein and less damage to venous wall, and can effectively avoid forming in-stent secondary thrombosis after intravascular stent implantation.

(Continued)

Moreover, the intravascular stent of the present disclosure can be well positioned in the iliac vein to improve the accuracy of the release, and it is simple for operation. The vascular stent of the present disclosure has the advantages of simple structure, convenient production and low cost, and thereby has important practical significance and good prospect in clinical application.

13 Claims, 11 Drawing Sheets

(30) Foreign Application Priority Data

| Apr. 27, 2016 | (CN) | 201610268834.X |
|---|---|---|
| Apr. 27, 2016 | (CN) | 201610268908.X |
| Jul. 6, 2016 | (CN) | 201610525145.2 |

(51) Int. Cl.
*A61F 2/06* (2013.01)
*A61F 2/00* (2006.01)
*A61F 2/82* (2013.01)

(52) U.S. Cl.
CPC . *A61F 2002/0081* (2013.01); *A61F 2002/821* (2013.01); *A61F 2002/91525* (2013.01); *A61F 2002/91575* (2013.01); *A61F 2210/0004* (2013.01); *A61F 2210/0014* (2013.01); *A61F 2250/0015* (2013.01); *A61F 2250/0037* (2013.01); *A61F 2250/0039* (2013.01)

(56) References Cited

U.S. PATENT DOCUMENTS

| 2002/0169498 | A1 | 11/2002 | Kim et al. | |
| 2004/0111147 | A1* | 6/2004 | Rabkin | A61F 2/91 623/1.15 |
| 2005/0149166 | A1 | 7/2005 | Schaeffer | |
| 2007/0055358 | A1* | 3/2007 | Krolik | A61F 2/915 623/1.31 |
| 2007/0088428 | A1 | 4/2007 | Teichman | |
| 2007/0119295 | A1 | 5/2007 | McCullagh et al. | |
| 2008/0183273 | A1 | 7/2008 | Mesana et al. | |
| 2013/0325141 | A1* | 12/2013 | Gill | A61F 2/90 623/23.7 |

FOREIGN PATENT DOCUMENTS

| CN | 2724662 | 9/2005 |
| CN | 1691924 | 11/2005 |
| CN | 1726885 | 2/2006 |
| CN | 1816367 | 8/2006 |
| CN | 2917584 | 7/2007 |
| CN | 201085705 | 7/2008 |
| CN | 201200504 | 3/2009 |
| CN | 102481186 | 5/2012 |
| CN | 203089465 | 7/2013 |
| CN | 103230310 | 8/2013 |
| CN | 203408130 | 1/2014 |
| CN | 203988521 | 12/2014 |
| CN | 204446195 | 7/2015 |
| CN | 105250059 | 1/2016 |
| CN | 105726174 | 7/2016 |
| CN | 105726178 | 7/2016 |
| WO | 2005027789 | 3/2005 |
| WO | 2015147381 | 10/2015 |

* cited by examiner

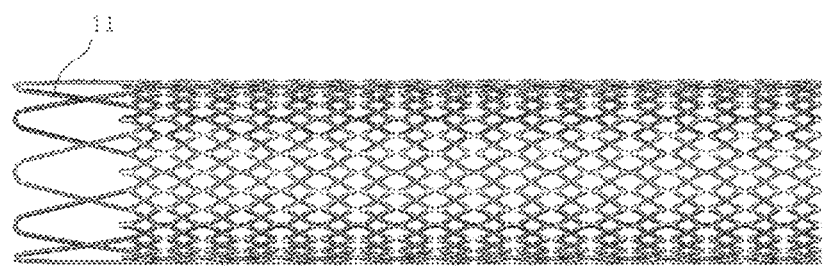
Fig. 3
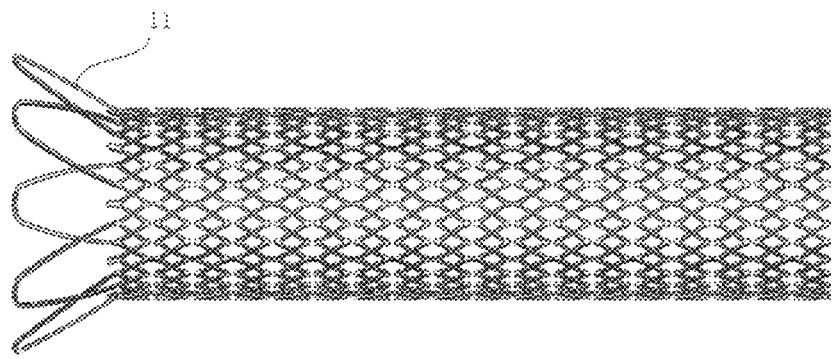
Fig. 4
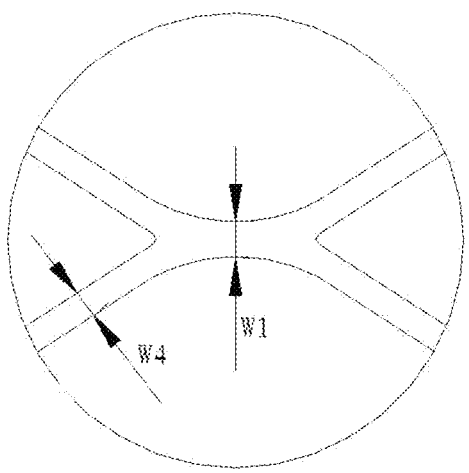 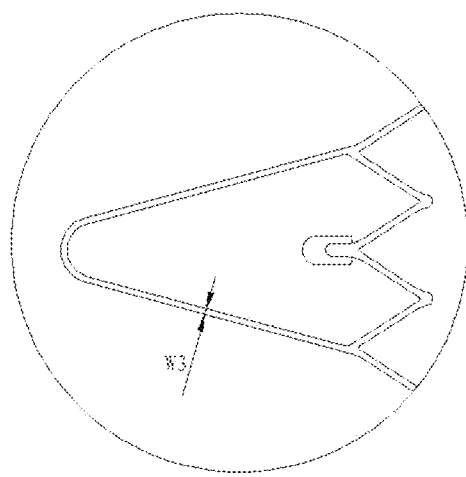
Fig. 5 Fig. 6

INTRAVASCULAR STENT, PREPARATION METHOD AND USE THEREOF

This application is a continuation-in-part of and claims the benefit of U.S. patent application Ser. No. 15/737,365, Filed Dec. 18, 2017, which is, itself, a § 371 National Stage Application of PCT/CN2016/089590, filed Jul. 11, 2016, which claims priority to CN201610267898.8, filed Apr. 27, 2016, and CN201610268333.1, filed Apr. 27, 2016, and CN201610268834.X, filed Apr. 27, 2016, and CN201610268908.X, filed Apr. 27, 2016, and CN201610525145.2 filed Jul. 6, 2016, which are incorporate by reference in their entirety.

TECHNICAL FIELD OF THE INVENTION

The present disclosure belongs to the field of medical apparatus and instruments, specifically to an intravascular stent, preparation method and use thereof.

BACKGROUND OF THE INVENTION

Venous disease is most common in vascular surgical diseases, especially lower extremity deep vein thrombosis and lower extremity great saphenous vein varicosity are even more common. And a big reason for the cause of the formation of these two diseases is that it is caused by iliac vein compression. Iliac vein compression syndrome (IVCS) refers to that iliac vein is compressed by iliac artery, leading to intracavity adhesion, stenosis or occlusion, thereby resulting in a series of clinical symptoms of the syndrome, also known as May-Thurner, Cockett syndrome. The incidence of iliac vein compression syndrome is in 20% to 34%.

Venous compression has always been solved by operation in the treatment, which has been difficult to be accepted by patients due to the need for abdominal surgery and large trauma, so the number of cases reported in China is few. It results in that lower extremity swelling of many patients can not be resolved, and some patients suffer venous thrombosis due to blood stasis. Since the 1990s, with the development of interventional technology, iliac vein compression has been solved by balloon dilatation and stent implantation in China, and after nearly 20 years of clinical treatment, interventional therapy has been accepted by the vascular surgery field, and due to small trauma, it can also be accepted by patients, and many hospitals have carried out this work in China now. There are also many physicians who use this technique for patients with sequelae of iliac vein thrombosis. With the great increase in the number of clinical cases, now the arterial stent with large bore is used to treat patients with iliac vein compression syndrome in clinic, and thus an important issue appears, that is, there is a high risk of in-stent secondary thrombus, which is caused by that the arterial stent mesh is small, the arterial stent should be extended into the inferior vena cava for 1-1.5 cm due to the structure of iliac vein, and its supporting force is not designed for the vein.

At present, many Chinese and foreign research reports show that there is few stent designed for the iliac vein compression syndrome. In China, a removeable self-expanding iliac venous stent (utility model: 201520126120.6) effectively prevents pulmonary embolism caused by shed off of lower extremity deep vein clots, and after the achievement of treatment purposes, it can be removed via the jugular vein or femoral vein pathway to avoid complications resulted from stent long-term staying. A stent for the treatment of iliac vein stenosis (utility model: 201320053442.3) is woven by nickel-titanium wires into a latticed reticulated tube, the orifice of the front end of the reticulated tube is a bevel, an angle between the bevel and the cross section of the reticulated tube is 40 degrees, the reticulated tube has an oval mark ring thereon, to realize the accurate positioning. However, these iliac venous stents still have some problems: both are not suitable for the recovery of iliac venous blood flow and the increase of blood flow volume, and they easily lead to the formation of thrombosis, thus, it is necessary to carry out the research and development of new iliac venous stent as well as the application research thereof.

SUMMARY OF THE INVENTION

The technical problem to be solved by the present disclosure is to overcome the disadvantage of the prior art, and to provide intravascular stents of different structures, preparation methods and uses thereof, the intravascular stents having the following advantages: not easy to form thrombus, good tissue compatibility, appropriate support for vein and not affecting blood flow, easy to operate, accurate for positioning, and able to meet the clinical needs of iliac vein treatment.

To solve the above technical problems, the present disclosure employs the following technical schemes:

One aim of the present disclosure is to provide an intravascular stent capable of changing to an expanded state with an expanded second cross-sectional diameter from a compressed state with a first cross-sectional diameter, the intravascular stent comprises a positioning segment and a supporting segment connected in the axial direction of the intravascular stent, the positioning segment comprises a plurality of first repeating elements distributed in the circumferential direction along the intravascular stent, the supporting segment comprises at least two supporting units and at least one connecting unit connected in the axial direction of the intravascular stent, the supporting unit comprising a plurality of second repeating elements distributed in the circumferential direction along the intravascular stent, the number of the first repeating elements differs from the number of the second repeating elements, and a plane formed by front ends of the plurality of first repeating elements is vertical to or intersects with the axis of the intravascular stent.

In the present disclosure, the supporting units are alternate with the connecting units, that is, two ends of the connecting unit are connected with the supporting unit, respectively.

According to an implementation of the present disclosure, the number of the first repeating elements is less than the number of the second repeating elements.

Preferably, the number of the second repeating elements is 2-4 times larger than the number of the first repeating elements, and the number of the first repeating elements is 4 to 10.

Further, a front end of the supporting segment is connected with a first developing unit.

More further, a rear end of the supporting segment is connected with a plurality of second developing units, the number of the second developing units being 3 to 10.

Preferably, the number of the first developing units is equal to the number of the second developing units.

According to a preferred aspect of the present disclosure, the front end of the second repeating element of the supporting segment is connected with the first developing unit, and the number of the first developing units and the number of the first repeating elements may be or may not be equal.

In the present disclosure, the first repeating element may be connected with the second repeating element, or may be connected with the connecting unit.

According to a preferred aspect of the present disclosure, the front end of the first repeating element is a rounded corner, the radius of the inner arc of the rounded corner being larger than or equal to 0.1 mm.

Preferably, an angle between the plane formed by the front ends of the plurality of first repeating elements and the axis of the intravascular stent is 45°~89°.

According to an implementation of the present disclosure, an angle between the extending direction of the positioning segment and the axis of the intravascular stent is 0°~60°.

In particular, when the angle between the extending direction of the positioning segment and the axis of the intravascular stent is 0°, the intravascular stent is substantially cylinder-shaped; when there is an angle between the extending direction of the positioning segment and the axis of the intravascular stent, the positioning segment extends gradually facing away from the axial direction of the intravascular stent towards the front end from the end connected with the supporting segment.

According to a preferred aspect of the present disclosure, the length of the first repeating element is 5-15 mm, preferably 10-15 mm, the length of the supporting segment is 40-140 mm, preferably 60-120 mm, and the thickness of the intravascular stent is 0.1-0.3 mm.

According to an implementation of the present disclosure, the length of the second repeating element is 1-7 mm, preferably 2-5 mm.

According to a specific implementation of the present disclosure, the connecting unit comprises a plurality of connectors distributed in the circumferential direction along the intravascular stent, the number of the connectors being not more than the number of the second repeating elements, and the width of the connector being 0.1-0.3 mm.

In the present disclosure, the width of the connector is equal to the width of the first repeating element.

In the present disclosure, the width of the second repeating element may employ a conventional width, for example, 0.1-0.3 mm.

In the present disclosure, the material of the intravascular stent is one or more selected from stainless steel, memory alloy, nickel-titanium alloy, titanium alloy, tantalum alloy, cobalt-chromium alloy, biodegradable metal, biodegradable polymer, magnesium alloy, pure iron.

The second aim of the present disclosure is to provide an intravascular stent, capable of changing to an expanded state with an expanded second cross-sectional diameter from a compressed state with a first cross-sectional diameter, wherein, the intravascular stent comprises a positioning segment and a supporting segment connected in the axial direction of the intravascular stent, the positioning segment comprises a plurality of first repeating elements distributed in the circumferential direction along the intravascular stent, the supporting segment comprises at least two supporting units and at least one connecting unit connected in the axial direction of the intravascular stent, the at least two supporting units each comprising a plurality of second repeating elements distributed in the circumferential direction along the intravascular stent, the number of the first repeating elements differs from the number of the second repeating elements of each of the at least two supporting units, and the second repeating elements of the supporting unit located at front ends and rear ends of the supporting segments are one-to-one correspondingly connected with the second repeating elements of another adjacent supporting unit to form close-loop structures.

According to an implementation of the present disclosure, holes formed by the first repeating elements are larger than holes formed by the second repeating elements in size so as to avoid the formation of thrombosis caused by a small hole of the intravascular stent or effect on the blood flow of the opposite iliac vein caused by the positioning segment.

According to an implementation of the present disclosure, the number of the first repeating elements is less than the number of the second repeating elements of each of the at least two supporting units.

Preferably, the number of the second repeating elements is 2-4 times larger than the number of the first repeating elements, and the number of the first repeating elements is 4 to 10.

Further, a front end of the supporting segment is connected with a plurality of first developing units.

More further, the number of the first developing units is 3 to 10.

Further, a rear end of the supporting segment is connected with a plurality of second developing units.

More preferably, the number of the second developing units is 3 to 10.

Further, a front end of the positioning segment is connected with a plurality of third developing units.

More further, the number of the third developing units is 3 to 10.

More preferably, the number of the first developing units is equal to the number of the second developing units.

More preferably, the number of the first developing units is equal to the number of the third developing units.

According to a preferred aspect of the present disclosure, the front end of the second repeating element of the supporting segment is connected with the first developing unit, and the number of the first developing units and the number of the first repeating element may be or may not be equal.

In the present disclosure, the first repeating element may be connected with the second repeating element, or may be connected with the connecting unit.

According to an implementation of the present disclosure, an angle between the extending direction of the positioning segment and the axis of the intravascular stent is 0°~60°.

Preferably, when the angle between the extending direction of the positioning segment and the axis of the intravascular stent is 0°, the intravascular stent is substantially cylinder-shaped; when there is an angle between the extending direction of the positioning segment and the axis of the intravascular stent, the positioning segment extends gradually facing away from the axial direction of the intravascular stent towards the front end from the end connected with the supporting segment.

According to a preferred aspect of the present disclosure, the front end of the first repeating element is a rounded corner, the radius of the inner arc of the rounded corner is larger than or equal to 0.1 mm.

According to a preferred aspect of the present disclosure, a length of the first repeating element is 5-15 mm, preferably 10-15 mm; a length of the supporting segment is 40-140 mm, preferably 60-120 mm; and a thickness of the intravascular stent is 0.1-0.3 mm.

According to an implementation of the present disclosure, a length of the second repeating element is 1-7 mm, preferably 2-5 mm.

According to a specific implementation of the present disclosure, the at least one connecting unit comprises a plurality of connectors distributed in the circumferential direction along the intravascular stent, the number of the connectors being not more than the number of the second repeating elements.

According to an advantageous embodiment, the number of the connectors of the connecting unit located at front ends and rear ends of the supporting segments is equal to the number of the second repeating elements of the supporting units located at front ends and rear ends of the supporting segments, and the number of the connectors of the connecting unit located in the middle portion of the supporting segments is less than the number of the second repeating elements of the supporting units located in the middle portion of the supporting segment.

According to another advantageous embodiment, the supporting segment comprises a first supporting part, a second supporting part and a third supporting part connected successively in the axial direction of the intravascular stent, and the positioning segment is connected with the first supporting part, the structure formed by two adjacent second repeating elements of the first supporting part is alternately arranged by closed-loop and open-loop in the axial direction.

Further, the structure formed by two adjacent second repeating elements of the second supporting part is open-loop.

Further, the length of the first supporting part accounts for 0.4-0.6 of the total length of the supporting segment.

Further, the length of the third supporting part accounts for 0.05-0.15 of the total length of the supporting segment.

More further, in the first support part, when viewed from front to back in the axial direction of the stent, the number of the connectors in an odd-numbered row is equal to the number of the second repeating elements of the supporting units in the adjacent row, and the number of the connectors in an even-numbered row is smaller than the number of the second repeating elements of the supporting units in the adjacent row.

More further, in the second support part, the number of the connectors of the connecting unit is less than the number of the second repeating elements of the supporting units.

Preferably, a width of the plurality of connectors is 0.1-0.3 mm.

According to another advantageous embodiment, the width of the plurality of connectors is equal to the width of the plurality of first repeating elements.

According to another advantageous embodiment, a width of the plurality of second repeating elements may employ a conventional width, for example, 0.1-0.3 mm.

According to a specific implementation of the present disclosure, the plane formed by the front ends of the plurality of first repeating elements is vertical to the axis of the intravascular stent.

According to a specific implementation of the present disclosure, an angle between the plane formed by the front ends of the plurality of first repeating elements and the axis of the intravascular stent is 45°~89°.

In the present disclosure, the material of the intravascular stent is one or more selected from stainless steel, memory alloy, nickel-titanium alloy, titanium alloy, tantalum alloy, cobalt-chromium alloy, biodegradable metal, biodegradable polymer, magnesium alloy, pure iron.

The third aim of the present disclosure is to provide an intravascular stent capable of changing to an expanded state with an expanded second cross-sectional diameter from a compressed state with a first cross-sectional diameter, the intravascular stent comprises a positioning segment, a central supporting segment and an end supporting segment connected successively in the axial direction of the intravascular stent, the positioning segment comprises a plurality of first repeating elements distributed in the circumferential direction along the intravascular stent, the central supporting segment comprises at least two central supporting units and at least one first connecting unit connected in the axial direction of the intravascular stent, the central supporting unit comprising a plurality of second repeating elements distributed in the circumferential direction along the intravascular stent, the end supporting segment comprises at least two end supporting units and at least one second connecting unit connected in the axial direction of the intravascular stent, the end supporting unit comprising a plurality of third repeating elements distributed in the circumferential direction along the intravascular stent, the number of the first repeating elements differs from the number of the second repeating elements, the supporting force of the central supporting segment is larger than the supporting force of the end supporting segment, and a plane formed by front ends of the plurality of first repeating elements is vertical to or intersects with the axis of the intravascular stent.

In the present disclosure, the central supporting units are alternate with the first connecting units, that is, two ends of the first connecting unit are connected with the central supporting unit, respectively, and the arrangement between the end supporting units and the second connecting units are the same to the arrangement between the central supporting units and the first connecting units.

According to an implementation of the present disclosure, the number of the first repeating elements is less than the number of the second repeating elements.

Preferably, the number of the second repeating elements is 2-4 times larger than the number of the first repeating elements, and the number of the first repeating elements is 4 to 10.

Further, a front end of the central supporting segment is connected with a first developing unit.

More further, a rear end of the end supporting segment is connected with a plurality of second developing units, the number of the second developing units being 3 to 10.

Preferably, the number of the first developing units is equal to the number of the second developing units.

According to a preferred aspect of the present disclosure, the front end of the second repeating element of the central supporting segment is connected with the first developing unit, and the number of the first developing units and the number of the first repeating element may be or may not be equal.

In the present disclosure, the first repeating element may be connected with the second repeating element, or may be connected with the first connecting unit.

According to an implementation of the present disclosure, an angle between the extending direction of the positioning segment and the axis of the intravascular stent is 0°~60°.

Preferably, when the angle between the extending direction of the positioning segment and the axis of the intravascular stent is 0°, the intravascular stent is substantially cylinder-shaped; when there is an angle between the extending direction of the positioning segment and the axis of the intravascular stent, the positioning segment extends gradually facing away from the axial direction of the intravascular stent towards the front end from the end connected with the central supporting segment.

According to a preferred aspect of the present disclosure, the front end of the first repeating element is a rounded corner, the radius of the inner arc of the rounded corner being larger than or equal to OA mm.

According to a preferred aspect of the present disclosure, the length of the first repeating elements is 5-15 mm, preferably 10-15 mm; the lengths of the central supporting segment and the end supporting segment are independently 20-70 mm, preferably 30-60 mm; and the thickness of the intravascular stent is 0.1-0.3 mm.

According to an implementation of the present disclosure, the lengths of the second repeating element and the third repeating element are independently 1-7 mm, preferably 2-5 mm.

According to a specific implementation of the present disclosure, the first connecting unit comprises a plurality of first connectors distributed in the circumferential direction along the intravascular stent, the second connecting unit comprises a plurality of second connectors distributed in the circumferential direction along the intravascular stent, the number of the first connectors is not more than the number of the second repeating elements, the number of the second connectors is not more than the number of the third repeating elements, and the number of the second repeating elements is equal to the number of the third repeating elements.

Preferably, the number of the first connectors is equal to the number of the second connectors.

More preferably, the number of the second repeating elements in each central supporting unit is 2-3 times larger than the number of the first connectors in each first connecting unit.

More preferably, the number of the third repeating elements in each end supporting unit is 2-3 times larger than the number of the second connectors in each second connecting unit.

In the present disclosure, the central supporting segment and the end supporting segment may be connected with the end supporting unit via the first connecting unit, or may be connected with the second connecting unit by using the central supporting unit.

Preferably, the width of the first connector is wider than the width of the second connector by 10%-30%, and the width of the second connector is 0.1-0.3 mm.

In the present disclosure, the width of the first connector is equal to the width of the first repeating element.

In the present disclosure, the width of the second repeating element and the width of the third repeating element may employ a conventional width, for example, 0.1-0.3 mm.

According to a specific implementation of the present disclosure, an angle between the plane formed by the front ends of the plurality of first repeating elements and the axis of the intravascular stent is 45°~89°.

In the present disclosure, the material of the intravascular stent is one or more selected from stainless steel, memory alloy, nickel-titanium alloy, titanium alloy, tantalum alloy, cobalt-chromium alloy, biodegradable metal, biodegradable polymer, magnesium alloy, pure iron.

The third aim of the present disclosure is to provide a preparation method of the intravascular stent comprising, laser cutting the material in accordance with a path on a stent design drawing, and then pickling and electrochemical treating to obtain the vascular stent.

Of course, the intravascular stent of the present disclosure may employ other methods to manufacture, for example, weaving or welding.

The fourth aim of the present disclosure is to provide a stent delivery system, which comprises the above intravascular stent.

The fifth aim of the present disclosure is to provide use of the intravascular stent in bifurcation vessel.

The sixth aim of the present disclosure is to provide use of the intravascular stent in iliac vein.

In the present disclosure, the side where the positioning segment is located is defined as the front of the intravascular stent.

In the present disclosure, the defined angle is an angle less than 90° formed between a straight line and a plane or between two straight lines.

In the present disclosure, the total length of the intravascular stent is the longest vertical distance between the front end of the first repeating element and the second developing unit. The lengths of the first repeating elements, the second repeating elements and the third repeating elements refer to the vertical distances from the front end to the rear end of each element. The length of the supporting segment refers to the vertical distance between the first developing unit and the second developing unit. The length of the central supporting segment refers to the vertical distance between the first developing unit and the front end of the end supporting segment. The length of the end supporting segment refers to the vertical distance between the rear end of the central supporting segment and the second developing unit.

The beneficial effects of the present disclosure are:

The intravascular stent of the present disclosure is particularly suitable for iliac vein, with good supporting effect for iliac vein and small damage to venous wall, and can effectively avoid forming in-stent secondary thrombosis after intravascular stent implantation. Moreover, the intravascular stent of the present disclosure can be well positioned in the iliac vein to improve the accuracy of the release, and it is simple for operation. The vascular stent of the present disclosure has the advantages of simple structure, convenient production and low cost, and thereby has important practical significance and good prospect in clinical application.

BRIEF DESCRIPTION OF DRAWINGS

FIG. 3 is a space diagram of the intravascular stent of Embodiment 1 in the expanded state (the extending direction of the positioning segment is in accordance with the axial direction of the intravascular stent);

FIG. 4 is a space diagram of an intravascular stent of Embodiment 1 in the expanded state (the positioning segment is in a hydraucone shape);

FIG. 5 is an enlarged diagram of the first connector in Embodiments 1 and 2;

FIG. 6 is an enlarged diagram of the first repeating element in Embodiments 1 and 2;

DETAILED DESCRIPTION OF EMBODIMENTS

In the following, the present disclosure is further described in detail combining with specific embodiments, but is not limit to the following embodiments.

The intravascular stent of the present invention is mainly suitable for bifurcation vessel, in particular for iliac vein (as shown in FIGS. 1, 10-13, 23-26, and 35-37). During implanting the intravascular stent in iliac vein, the intravascular stent is mounted in a conveyor of a stent delivery system, and at present, the intravascular stent is in a compressed state, when the conveyor delivers the intravascular stent to an appropriate position and releases the intravascular stent, the intravascular stent expands outwards to an expanded state and thereby supports iliac vein, the intravascular stent has a first cross section in the compressed state, and a second cross section in the expanded state, and the diameter of the first cross section is less than the diameter of the second cross section. In the present invention, the first cross section and the second cross section are the cross sections of the supporting segment 2 or the central supporting segment 2, and the cross section is vertical to the axis of the intravascular stent. In the present invention, the external diameter of the second cross section is 10-20 mm, preferably 12-16 mm.

The material of the intravascular stent is one or more selected from stainless steel, memory alloy, nickel-titanium alloy, titanium alloy, tantalum alloy, cobalt-chromium alloy, biodegradable metal, biodegradable polymer, magnesium alloy, pure iron. The stainless steel employs SUS-316L stainless steel, or the like. The memory alloy may employ Ni—Ti alloy, Cu—Al—Mn alloy, or the like. The cobalt-chromium alloy may employ CoCr-L605 cobalt-chromium alloy. The biodegradable metal is a metal that would be decomposed in a human body, for example, pure magnesium, magnesium alloy, pure iron, ferroalloy and the like. The biodegradable polymer may be a polymer that would be biodegraded, such as polylactic acid, polyglycolic acid, poly (lactate-c-caprolactone), poly (glycolic acid-c-caprolactone)

and the like. Moreover, the biodegradable metal may be coated with a biodegradable polymer to serve as intravascular stent material.

The intravascular stent of the present disclosure may be one-step formed via laser engraving. The preparation process of laser engraving is: first, establishing a cutting path by utilizing CAM based on supports design drawing; next, laser cutting the metal or high molecular material; finally, pickling and electrochemical treating to improve the degree of finish of the surface and round the edge shape.

Embodiment 1, Embodiment 2, Embodiment 5 and Embodiment 6

Figure 2:
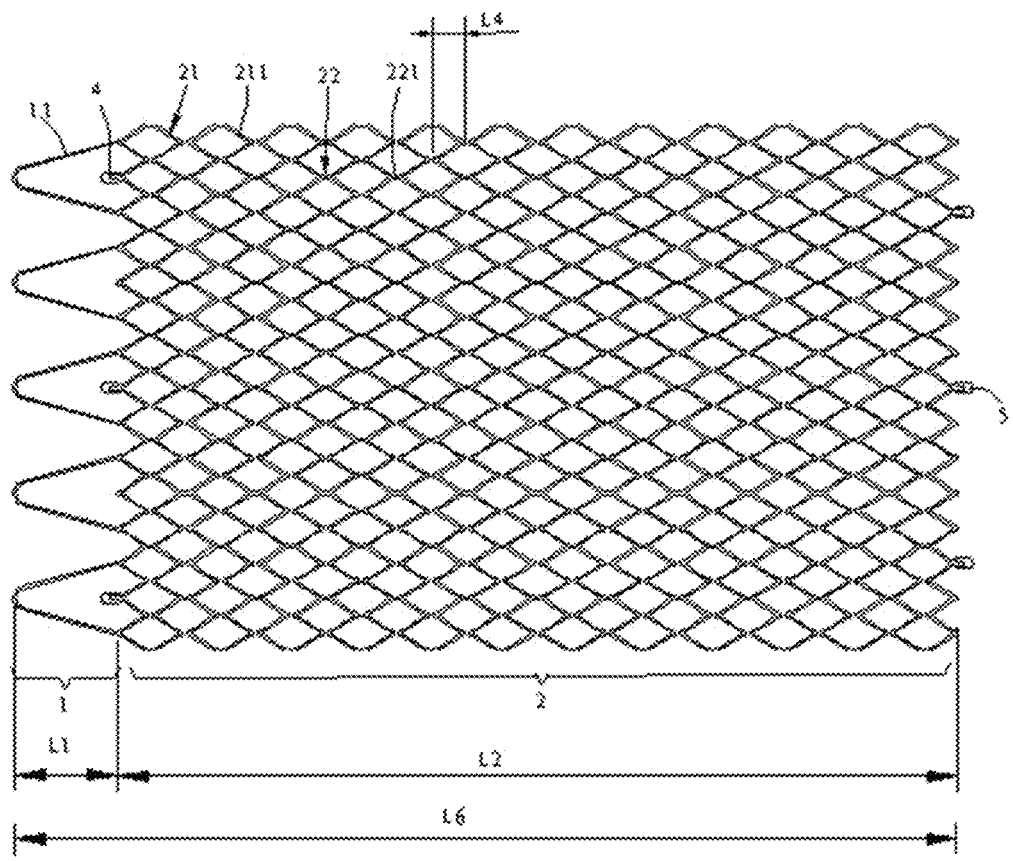
FIG. 2 is a schematic structure diagram of the intravascular stent of Embodiment 1 being unfolded to a plane.
Figure 27:
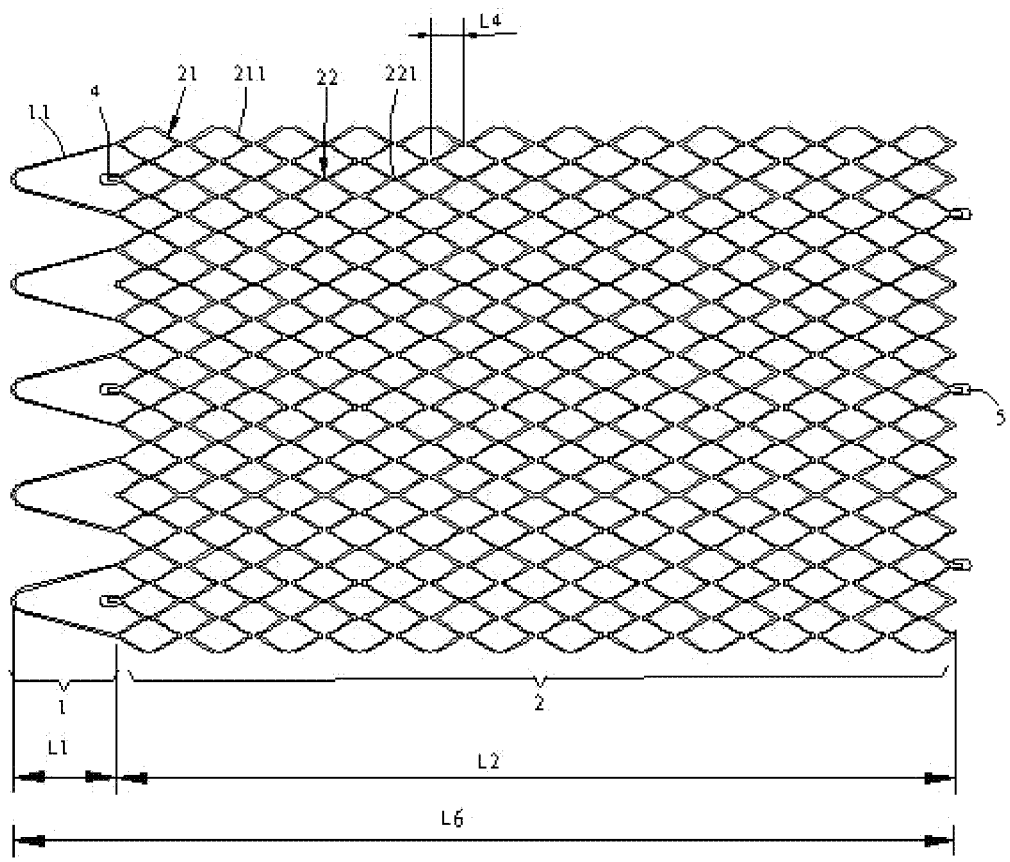
FIG. 27 is a schematic structure diagram of the intravascular stent of Embodiment 5 being unfolded to a plane.

As shown in FIGS. 2, 3 and 27, the intravascular stent comprises a positioning segment 1 and a supporting segment 2 connected from the front to the end in the axial direction of the intravascular stent.

The positioning segment 1 comprises a plurality of first repeating elements 11 distributed in the circumferential direction along the intravascular stent.

The supporting segment 2 comprises at least two supporting units 21 and at least one connecting unit 22 connected in the axial direction of the intravascular stent, the supporting unit 21 comprises a plurality of second repeating elements 211 distributed in the circumferential direction along the intravascular stent, and the connecting unit 22 comprises a plurality of connectors 221 distributed in the circumferential direction along the intravascular stent. The number of the connectors 221 is not more than the number of the second repeating elements 211.

The structures of the first repeating elements 11 and the second repeating elements 211 of the present invention may be any shape capable of forming holes, for example, V shape, grid shape, rhombus and the like. The distribution of the connectors 221 in the whole intravascular stent may be arbitrary, such as linear shaped, V shaped, W shaped, S shaped, N shaped and the like.

In the present invention, a front end of the supporting segment 2 is connected with a first developing unit 4, and in the present embodiment, a front end of the second repeating element 211 of the supporting segment 2 is connected with the first developing unit 4, and the arrangement of the first developing unit 4 causes good positioning of the intravascular stent to facilitate the doctor to find the release point.

In the present invention, the number of the first repeating elements 11 is 4 to 10, and the number of the first developing units 4 and the number of the first repeating elements 11 are equal or not equal.

In the present invention, a rear end of the supporting segment 2 is connected with a plurality of second developing units 5, the number of the second developing units 5 is 3 to 10, and the number of the second developing units 5 and the number of the first developing units 4 are equal. In the present embodiment, the second developing unit 5 may be connected with the supporting unit 21, or with the connecting unit 22, and the second developing units 5 are uniformly distributed in the circumferential direction along the intravascular stent.

Figure 1:
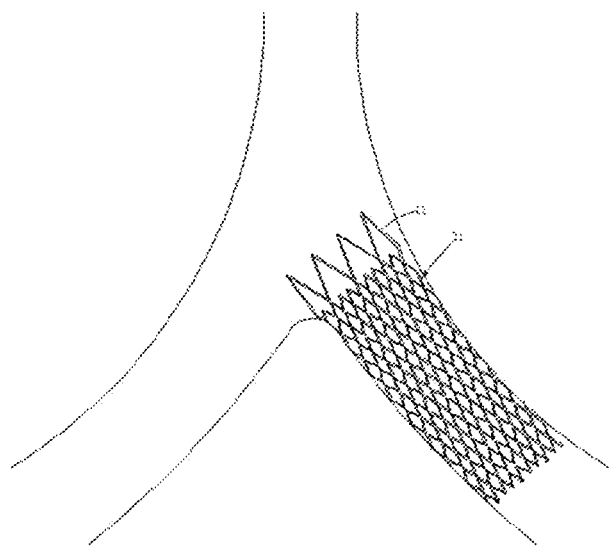
FIG. 1 is a schematic diagram of an intravascular stent of Embodiment 1 implanted in iliac vein (the extending direction of the positioning segment is in accordance with the axial direction of the intravascular stent)

In the present invention, the number of the first repeating elements 11 differs from the number of the second repeating elements 211. Preferably, the number of the first repeating elements 11 is less than the number of the second repeating elements 211, and in the present embodiment, the number of the second repeating elements 211 is 2-4 times larger than the number of the first repeating elements 11, so as to ensure large hole formed by the first repeating elements 11, and after implanting the intravascular stent in iliac vein as shown in FIG. 1, the formation of thrombosis caused by a small hole of the intravascular stent or effect on the blood flow of the opposite iliac vein caused by the positioning segment 1 can be avoid when the positioning segment 1 extends to inferior vena cava.

Figure 28:
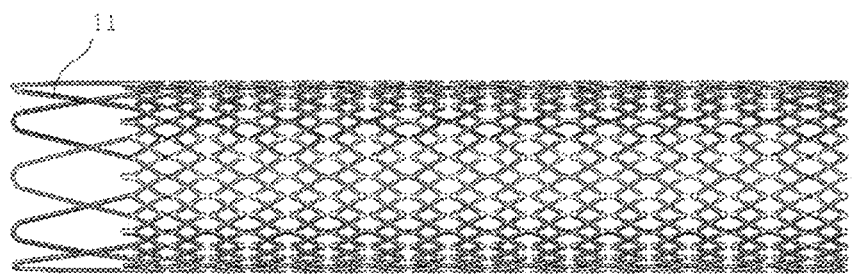
FIG. 28 is a space diagram of the intravascular stent of Embodiment 5 in the expanded state (the extending direction of the positioning segment is in accordance with the axial direction of the intravascular stent)
Figure 29:
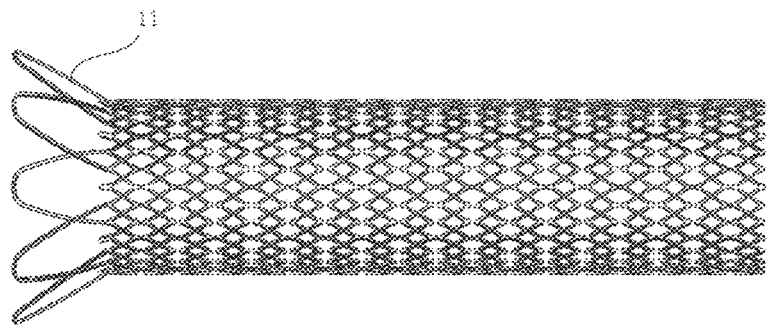
FIG. 29 is a space diagram of an intravascular stent of Embodiment 5 in the expanded state (the positioning segment is in a hydraucone shape)
Figure 30:
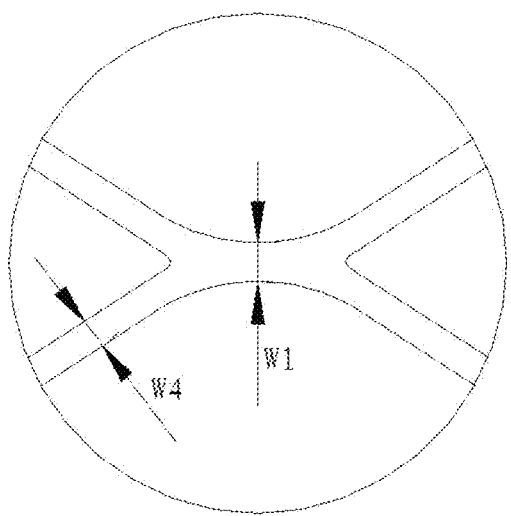
FIG. 30 is an enlarged diagram of the first connector in Embodiments 5 and 6.
Figure 31:
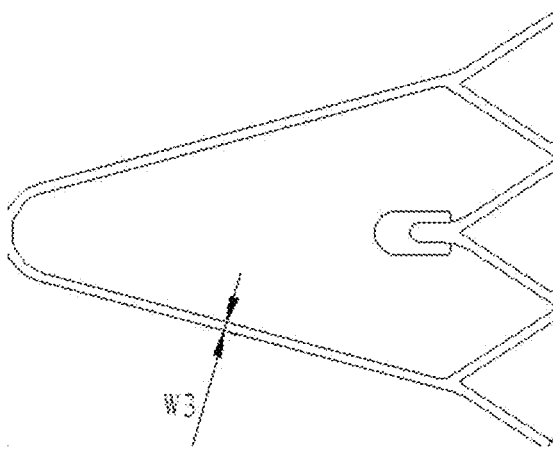
FIG. 31 is an enlarged diagram of the first repeating element in Embodiments 5 and 6.
Figure 32:
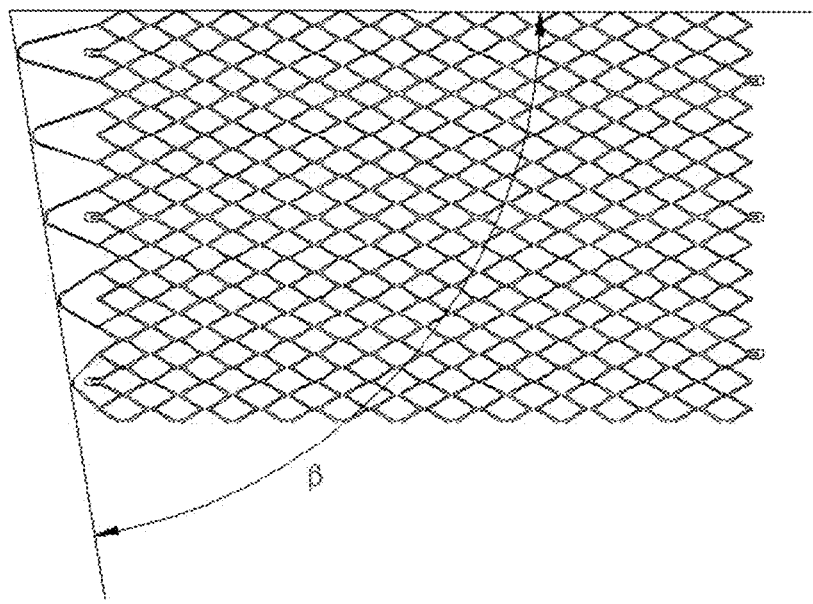
FIG. 32 is a schematic structure diagram of the intravascular stent of Embodiment 6 being unfolded to a plane.

In the present embodiment, an angle between the extending direction of the positioning segment 1 and the axis of the intravascular stent is 0°~60°. As shown in FIGS. 3 and 28, the extending direction of the positioning segment 1 is accordance with the axis of the intravascular stent, that is, the angle is 0°, and in this condition, the intravascular stent in the expanded state is substantially cylinder-shaped. As shown in FIGS. 4 and 29, there is an angle between the extending direction of the positioning segment 1 and the axis of the intravascular stent, and the positioning segment 1 extends gradually facing away from the axial direction of the intravascular stent towards the front end from the end connected with the supporting segment 2, that is, the positioning segment 1 is hydraucone-shaped expanded gradually from rear to front.

In the present embodiment, the width W1 of the connector 221 (as shown FIG. 5) is 0.1-0.3 mm. The width W1 of the connector 221 and the width W3 of the first repeating element 11 (as shown FIG. 6) are equal. The width W4 of the second repeating element 211 (as shown FIG. 5) may employ a conventional width, for example, 0.1-0.3 mm. And, the width of the connector 221 is equal to the width of the second repeating element 211.

In the present embodiment, the thickness of the intravascular stent is 0.1-0.3 mm (not shown), and the thickness of the intravascular stent refers to the difference between the external diameter and the inner diameter of the cross section of the intravascular stent.

In the present embodiment, the front end of the first repeating element 11 is a rounded corner, and the radius of the inner arc of the rounded corner is larger than 0.1 mm (not shown), so as to reduce the vascular stimulation from the intravascular stent.

In the present embodiment, the length L1 of the first repeating element 11 is 5-15 mm, preferably 10-15 mm, if the length of the first repeating element 11 is too long, it will cause the front ends of the first repeating elements 11 contact the opposite vessel wall and cause harmful effects such as vascular stimulation; if the length of the first repeating element 11 is too short, it will affect the positioning of the intravascular stent in iliac vein, so as to cause that the intravascular stent cannot be implanted in the desired position stably.

The length L2 of the supporting segment 2 is 40-140 mm, preferably 60-120 mm, and the length L4 of the second repeating element 211 is 1-7 mm, preferably 2-5 mm, That is, the supporting segment 2 comprises substantially sixteen supporting units 21, of course, the number of the supporting units 21 could be adjusted according to the actual requirement.

The total length L6 of intravascular stent in expanded state of the present invention is 50-120 mm, preferably 60-100 mm.

Figure 7:
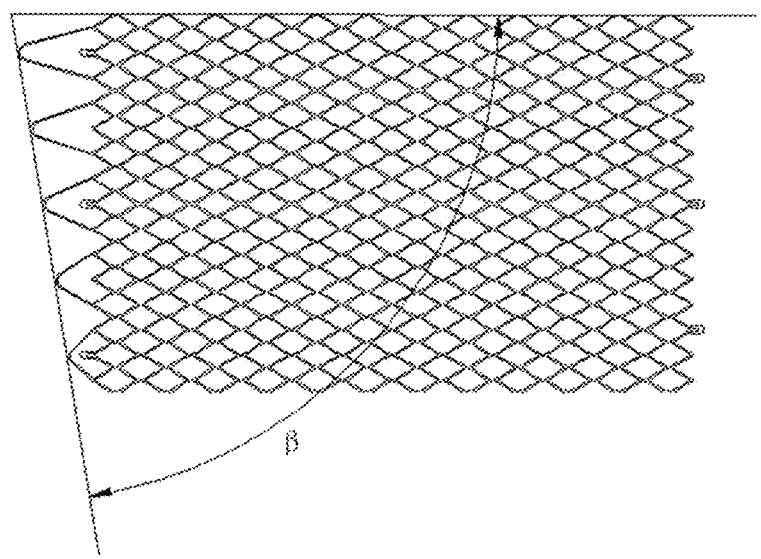
FIG. 7 is a schematic structure diagram of the intravascular stent of Embodiment 2 being unfolded to a plane.
Figure 8:
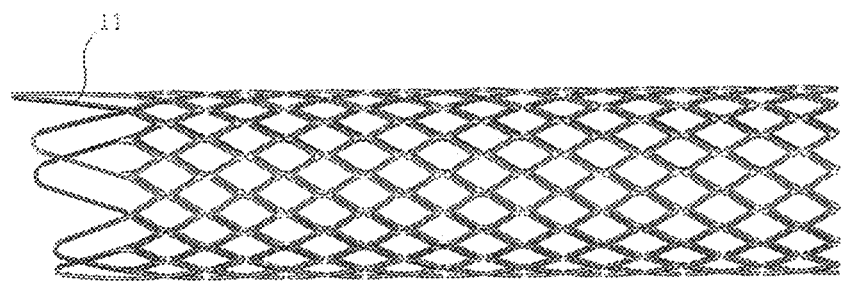
FIG. 8 is a space diagram of the intravascular stent of Embodiment 2 in the expanded state (the extending direction of the positioning segment is in accordance with the axial direction of the intravascular stent)
Figure 9:
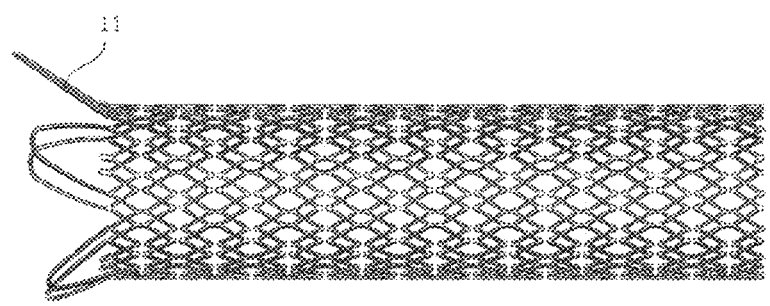
FIG. 9 is a space diagram of an intravascular stent of Embodiment 2 in the expanded state (the positioning segment is in a hydraucone shape)
Figures 10, 11:
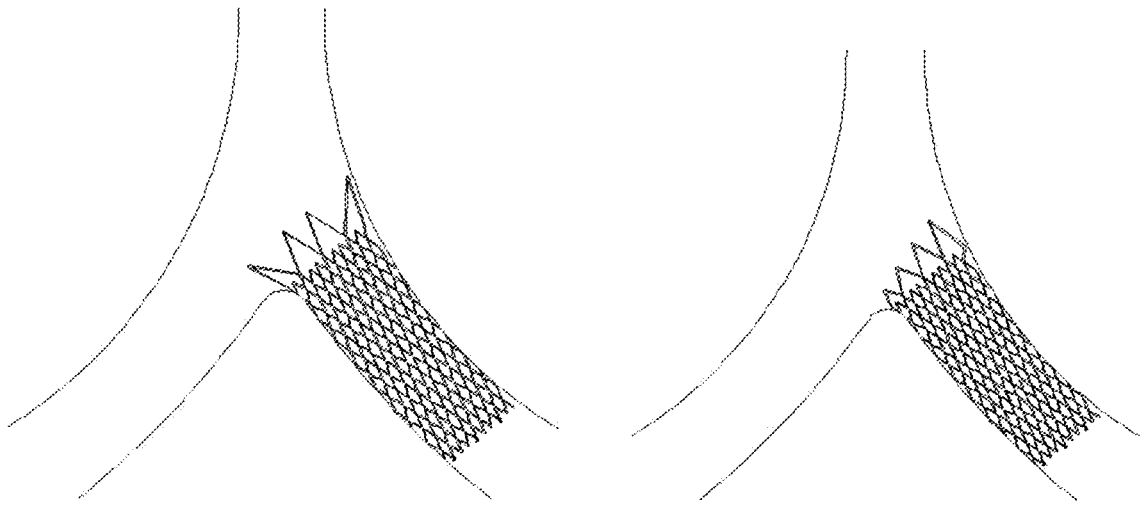
FIG. 10 is a schematic diagram of the intravascular stent of Embodiment 1 implanted in iliac vein (the positioning segment is in a hydraucone shape)
FIG. 11 is a schematic diagram of an intravascular stent of Embodiment 2 implanted in iliac vein (the extending direction of the positioning segment is in accordance with the axial direction of the intravascular stent)

The above mentioned contents of Embodiments 1 and 2 are the same, but differ in that: in Embodiment 1, the plane formed by the front ends of the plurality of the first repeating elements 11 is vertical to the axis of the intravascular stent, as shown in FIGS. 2 and 3. In Embodiment 2, the plane formed by the front ends of the plurality of the first repeating elements 11 intersects with the axis of the intravascular stent, and the angle β between the plane formed by the front ends of the plurality of the first repeating elements 11 and the axis of the intravascular stent is 45°-89°, as shown in FIGS. 7-9, wherein, in FIGS. 7-9, the angle β between the plane formed by the front ends of the plurality of the first repeating elements 11 and the axis of the intravascular stent is 70°, and in Embodiment 2, the lengths of the first repeating elements 11 vary gradually, however, the length range thereof should be in the above defined length range of the first repeating elements 11.

The above mentioned structures of Embodiments 1 and 5 are the same, the plane formed by the front ends of the plurality of the first repeating elements 11 is vertical to the axis of the intravascular stent, as shown in FIGS. 28 and 29.

Figure 33:
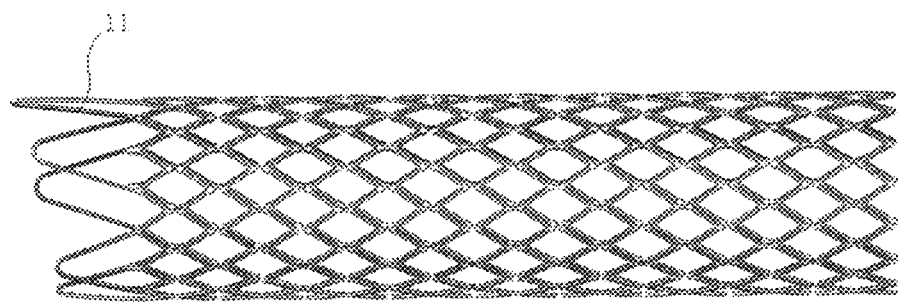
FIG. 33 is a space diagram of the intravascular stent of Embodiment 6 in the expanded state (the extending direction of the positioning segment is in accordance with the axial direction of the intravascular stent)
Figure 34:
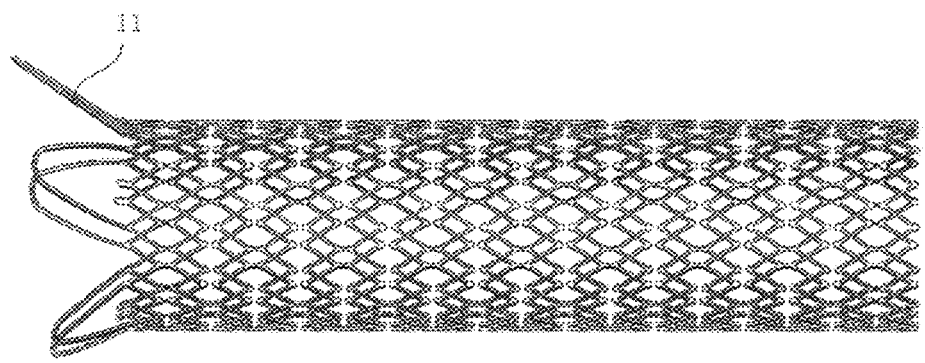
FIG. 34 is a space diagram of an intravascular stent of Embodiment 6 in the expanded state (the positioning segment is in a hydraucone shape)
Figure 35:
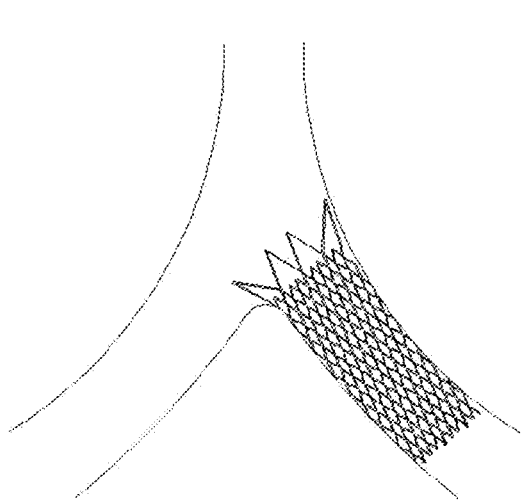
FIG. 35 is a schematic diagram of the intravascular stent of Embodiment 5 implanted in iliac vein (the positioning segment is in a hydraucone shape)
Figure 36:
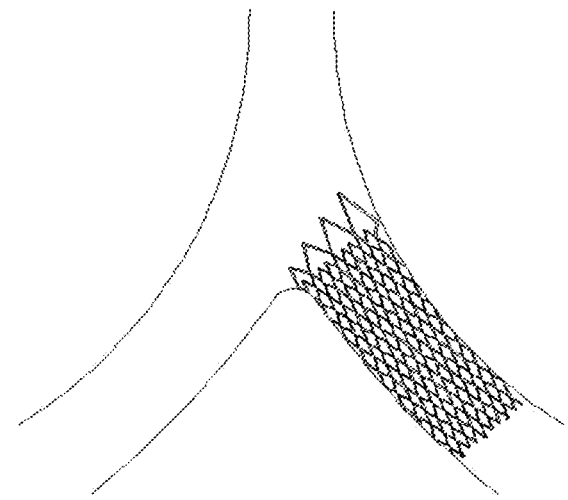
FIG. 36 is a schematic diagram of an intravascular stent of Embodiment 6 implanted in iliac vein (the extending direction of the positioning segment is in accordance with the axial direction of the intravascular stent)
Figure 37:
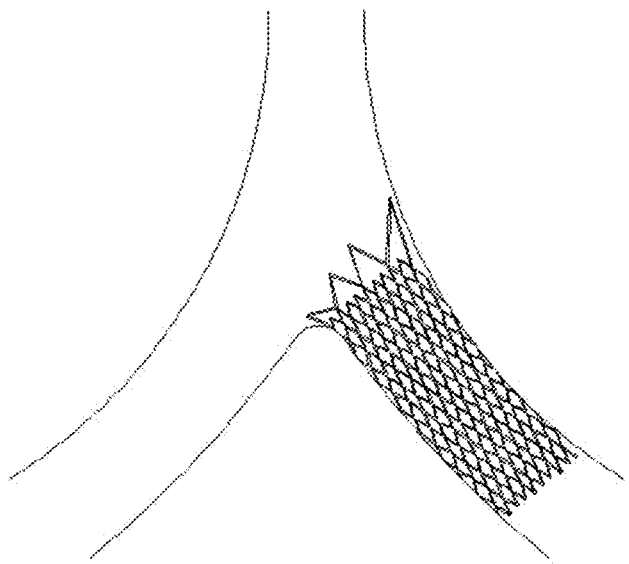
FIG. 37 is a schematic diagram of the intravascular stent of Embodiment 6 implanted in iliac vein (the positioning segment is in a hydraucone shape)

The above mentioned structures of Embodiments 2 and 6 are the same, the plane formed by the front ends of the plurality of the first repeating elements 11 intersects with the axis of the intravascular stent, and the angle β between the plane formed by the front ends of the plurality of the first repeating elements 11 and the axis of the intravascular stent is 45°-89°, as shown in FIGS. 33 and 34, wherein, in FIGS. 33 and 34, the angle β between the plane formed by the front ends of the plurality of the first repeating elements 11 and the axis of the intravascular stent is 70°, and in Embodiment 6, the lengths of the first repeating elements 11 vary gradually, however, the length range thereof should be in the above defined length range of the first repeating elements 11.

Embodiments 5, 6 and Embodiments 1, 2 differ by that: the second repeating elements 211 of the supporting unit 21 in Embodiments 1 and 2 form an open-loop structure, that is, in Embodiments 1 and 2, the number of the connectors 221 is less than the number of the second repeating elements 211, preferably, the number of the second repeating elements 211 in each supporting unit 21 is 2-3 times larger than the number of the connectors 221 in each connecting unit 22. In Embodiments 5 and 6, the second repeating elements 211 of the supporting unit 21 located at front ends and rear ends of the supporting segment 2 are one-to-one correspondingly connected with the second repeating elements 211 of another adjacent supporting unit 21 via the first connecting unit 22 to form close-loop structures, therefore, the number of the connectors 221 of the connecting unit 22 located at front ends and rear ends of the supporting segment 2 is equal to the number of the second repeating elements 211, and the number of the connectors 221 of the connecting unit 22 located in the middle of the supporting segment 2 is less than the number of the second repeating elements 211, preferably, the number of the second repeating elements 211 in each supporting unit 21 is 2-3 times larger than the number of the connectors 221 in each connecting unit 22. Therefore, the supporting units located in the middle of the supporting segment 2 is an open-loop structure. By forming the two ends of the supporting segment 2 into a close-loop structure and employing the open-loop structure in the center, it can well enhance the supporting force of the two ends, and is beneficial for the support uniformity and the expansion uniformity of the two ends after releasing the stent, so as to reduce the damage to vessel wall.

Figure 38:
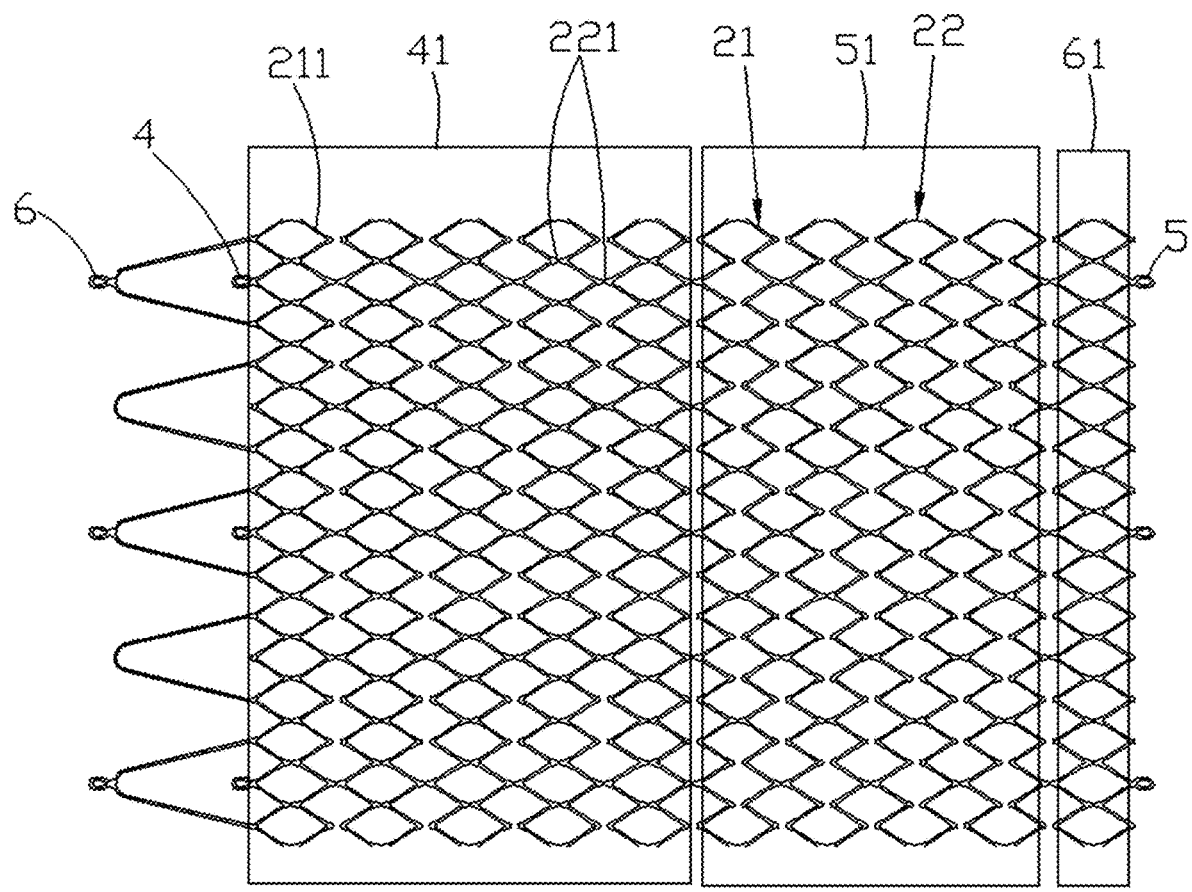
FIG. 38 is a schematic structure diagram of the intravascular stent of Embodiment 7 being unfolded to a plane.

The structure of embodiment 7 is substantially the same as that of embodiment 5 except for the point that it will be described in detail below, see FIG. 38.

A front end of the positioning segment 1 is connected with a plurality of third developing units 6, and the arrangement of the first developing unit 4 causes good positioning of the intravascular stent to facilitate the doctor to find the release point. The number of the third developing units 6 is 3 to 10.

The supporting segment 2 comprises a first supporting part 41, a second supporting part 51 and a third supporting part 61 connected successively in the axial direction of the intravascular stent, and the positioning segment 1 is connected with the first supporting part 41, the structure formed by two adjacent second repeating elements 211 of the first supporting part 41 is alternately arranged by closed-loop and open-loop in the axial direction, so that it can well enhance the supporting force of the first supporting part 41, so as to reduce the incidence of iliac vein stenosis or occlusion.

And the structure formed by two adjacent second repeating elements 211 of the second supporting part 51 is open-loop, so as to reduce the supporting force of the second supporting part 51 and prevent the iliac vein from being pressed by overlarge supporting force.

And the structure formed by two adjacent second repeating elements 211 of the third supporting part 61 is closed-loop, so as to uniformly expand the blood vessel stent; the vascular stent is convenient to install and release, and the stress of the blood vessel is uniform.

In other words, in the first support part 41, when viewed from front to back in the axial direction of the stent, the number of the connectors 221 in an odd-numbered row is equal to the number of the second repeating elements 211 of the supporting units 21 in the adjacent row, and the number of the connectors 221 in an even-numbered row is smaller than the number of the second repeating elements 211 of the supporting units 21 in the adjacent row. For example, the number of the connectors 221 in the first row is equal to the number of the second repeating elements 211 of the supporting units 21 in the adjacent row, and the number of the connectors 221 in the second row is less than the number of the second repeating elements 211 of the supporting units 21 in the adjacent row.

In the second support part 51, the number of the connectors 221 of the connecting unit 22 is less than the number of the second repeating elements 211 of the supporting units 21.

In the third support part 61, the number of the connectors 221 in each row is equal to the number of the second repeating elements 211 of the supporting units 21 in the adjacent row.

The length of the first supporting part 41 accounts for 0.4-0.6 of the total length of the supporting segment 2, the length of the third supporting part 61 accounts for 0.05-0.15 of the total length of the supporting segment 2.

Embodiment 3 and Embodiment 4

Figure 14:
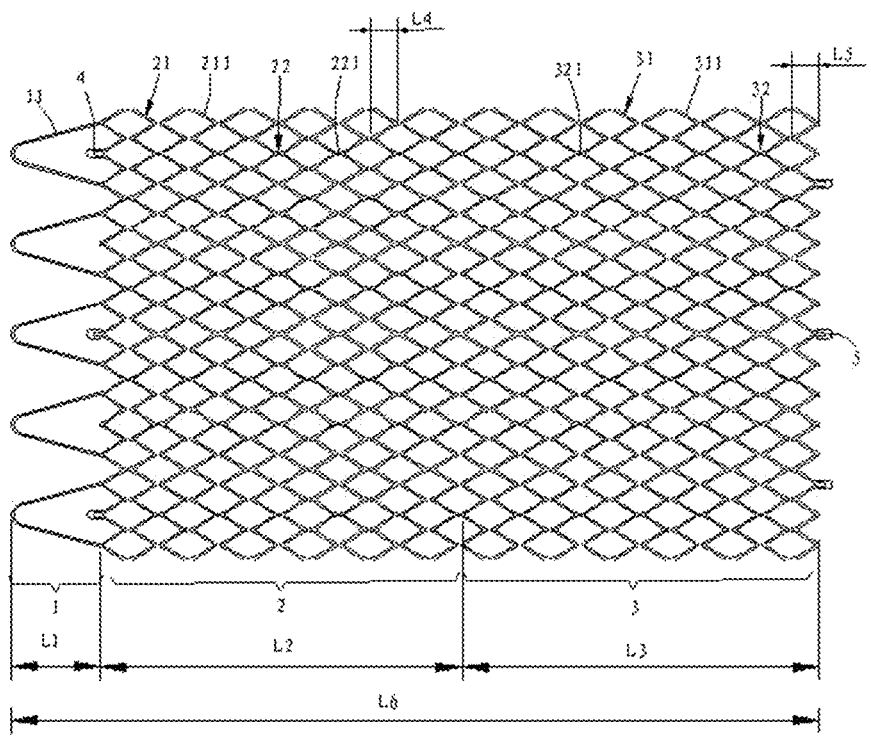
FIG. 14 is a schematic structure diagram of the intravascular stent of Embodiment 3 being unfolded to a plane.
Figure 15:
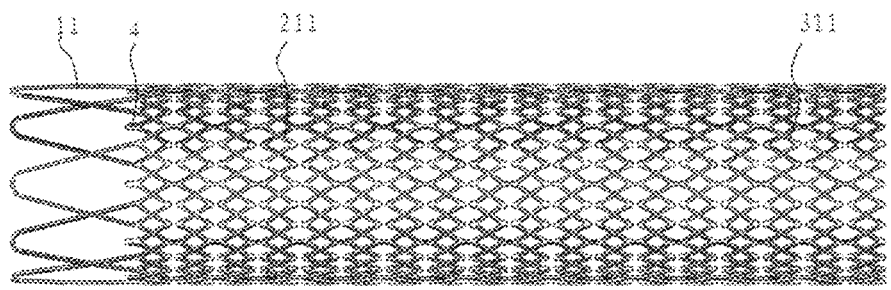
FIG. 15 is a space diagram of the intravascular stent of Embodiment 3 in the expanded state (the extending direction of the positioning segment is in accordance with the axial direction of the intravascular stent)

As shown in FIGS. 14 and 15, the intravascular stent comprises a positioning segment 1, a central supporting segment 2 and an end supporting segment 3 connected from the front to the end in the axial direction of the intravascular stent.

The positioning segment 1 comprises a plurality of first repeating elements 11 distributed in the circumferential direction along the intravascular stent.

The central supporting segment 2 comprises at least two central supporting units 21 and at least one first connecting unit 22 connected in the axial direction of the intravascular stent, the central supporting unit 21 comprises a plurality of second repeating elements 211 distributed in the circumferential direction along the intravascular stent, and the first connecting unit 22 comprises a plurality of first connectors 221 distributed in the circumferential direction along the intravascular stent. The number of the first connectors 221 is not more than the number of the second repeating elements 211, preferably, the number of the second repeating elements 211 in each central supporting unit 21 is 2-3 times larger than the number of the first connectors 221 in each first connecting unit 22.

The end supporting segment 3 comprises at least two end supporting units 31 and at least one second connecting unit 32 connected in the axial direction of the intravascular stent, the end supporting unit 31 comprises a plurality of third repeating elements 311 distributed in the circumferential direction along the intravascular stent, and the second connecting unit 32 comprises a plurality of second connectors 321 distributed in the circumferential direction along the intravascular stent. The number of the second connectors 321 is not more than the number of the third repeating elements 311, preferably, the number of the third repeating elements 311 in each end supporting unit 31 is 2-3 times larger than the number of the second connectors 321 in each second connecting unit 32. The number of the first connectors 221 is equal to the number of the second connectors 321.

The structures of the first repeating elements 11, the second repeating elements 211 and the third repeating elements 311 in the present invention may be any shape capable of forming holes, for example, V shape, grid shape, rhombus and the like. The distribution of the first connectors 221 and the second connectors 321 in the whole intravascular stent may be arbitrary, such as linear shaped, V shaped, W shaped, S shaped, N shaped and the like.

In the present embodiment, a front end of the central supporting segment 2 is connected with a first developing unit 4, and in the present embodiment, a front end of the second repeating element 211 of the central supporting segment 2 is connected with the first developing unit 4, and the arrangement of the first developing unit 4 causes good positioning of the intravascular stent to facilitate the doctor to find the release point.

In the present embodiment, the rear end of the first repeating elements 11 is connected with the front end of the second repeating elements 211.

In the present invention, the number of the first repeating elements 11 is 4 to 10, and the number of the first developing units 4 and the number of the first repeating elements 11 are equal or not equal.

In the present embodiment, the central supporting segment 2 and the end supporting segment 3 may be connected with the end supporting unit 31 via the first connecting unit 22, as well as with the second connecting unit 32 via the central supporting unit 21, that is, the connection between the central supporting segment 2 and the end supporting segment 3 may be the first connector 221, also may be the second connector 321. When the connection between the central supporting segment 2 and the end supporting segment 3 is the first connector 221, the number of the central supporting units 21 is equal to the number of the first connecting units 22.

In the present embodiment, a rear end of the end supporting segment 3 is connected with a plurality of second developing units 5, the number of the second developing units 5 is 3 to 10, and the number of the second developing units 5 and the number of the first developing units 4 are equal. In the present embodiment, the second developing unit 5 may be connected with the end supporting unit 31, or with the connecting unit 32, and the second developing units 5 are distributed in the circumferential direction along the intravascular stent.

Figures 12, 13:
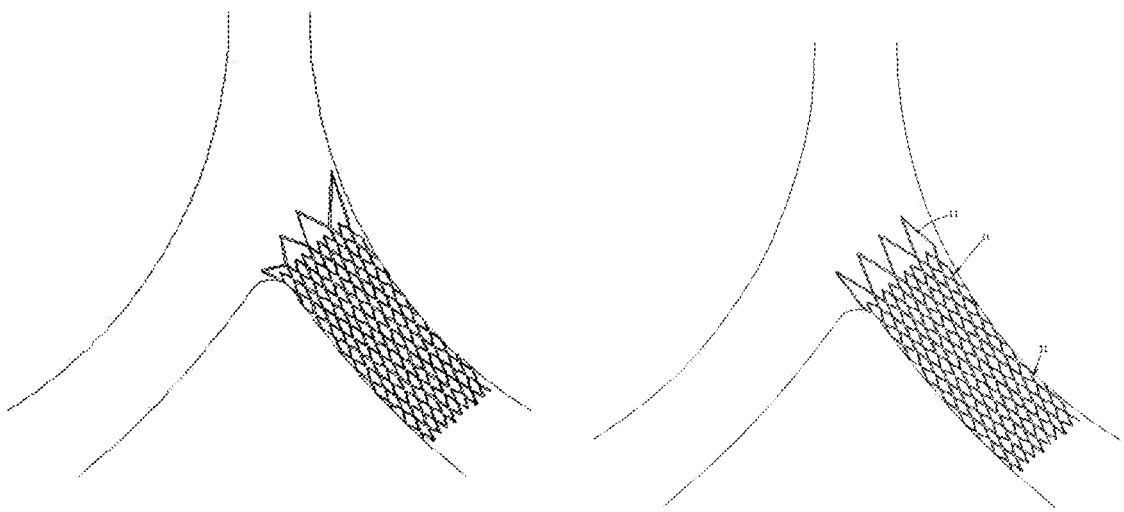
FIG. 12 is a schematic diagram of the intravascular stent of Embodiment 2 implanted in iliac vein (the positioning segment is in a hydraucone shape)
FIG. 13 is a schematic diagram of an intravascular stent of Embodiment 3 implanted in iliac vein (the extending direction of the positioning segment is in accordance with the axial direction of the intravascular stent)

In the present embodiment, the number of the first repeating elements 11 differs from the number of the second repeating elements 211, and the number of the second repeating elements 211 and the number of the third repeating elements 311 are equal. Preferably, the number of the first repeating elements 11 is less than the number of the second repeating elements 211, and in the present embodiment, the number of the second repeating elements 211 is 2-4 times larger than the number of the first repeating elements 11, so as to ensure large hole formed by the first repeating elements 11, and after implanting the intravascular stent in iliac vein as shown in FIG. 13, the formation of thrombosis caused by a small hole of the intravascular stent or effect on the blood flow of the opposite iliac vein caused by the positioning segment 1 can be avoid when the positioning segment 1 extends to inferior vena cava.

Figure 16:
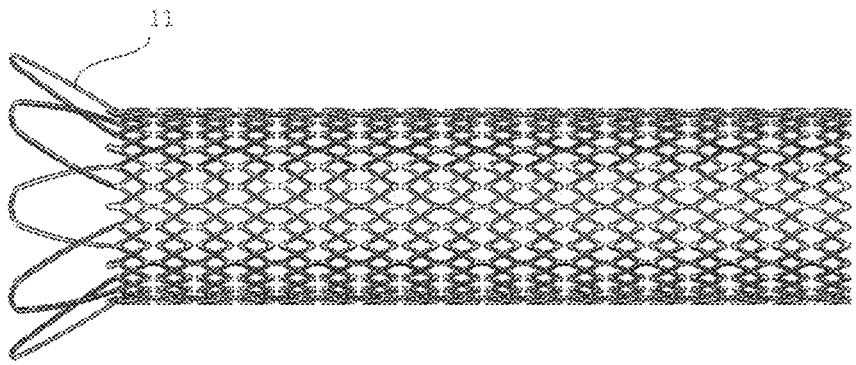
FIG. 16 is a space diagram of an intravascular stent of Embodiment 3 in the expanded state (the positioning segment is in a hydraucone shape)

In the present embodiment, an angle between the extending direction of the positioning segment 1 and the axis of the intravascular stent is 0°~60°. As shown in FIG. 15, the extending direction of the positioning segment 1 is accordance with the axis of the intravascular stent, that is, the angle is 0°, and in this condition, the intravascular stent in the expanded state is substantially cylinder-shaped. As shown in FIG. 16, there is an angle between the extending direction of the positioning segment 1 and the axis of the intravascular stent, and the positioning segment 1 extends gradually facing away from the axial direction of the intravascular stent towards the front end from the end connected with the supporting segment 2, that is, the positioning segment 1 is hydraucone-shaped expanded gradually from rear to front.

Figure 17:
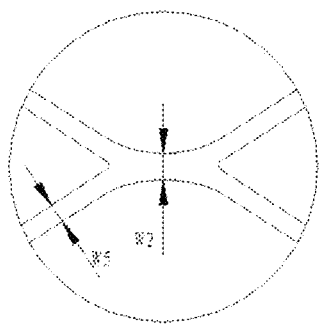
FIG. 17 is an enlarged diagram of the second connector in Embodiments 3 and 4.

In the present embodiment, the supporting force of the central supporting segment 2 is larger than the supporting force of the end supporting segment 3, which ensures the supporting force of the central supporting segment 2 of the intravascular stent to iliac vein, and meanwhile, reduces the damage of vein wall from the end supporting segment 3 of the intravascular stent. In the present embodiment, the width W1 of the first connector 221 is wider than the width W2 of the second connector 321 by 10%-30% to achieve that the supporting force of the central supporting segment 2 is larger than the supporting force of the end supporting segment 3, of course, other implementation may be employ to achieve that the supporting force of the central supporting segment 2 is larger than the supporting force of the end supporting segment 3. In the present embodiment, the width W2 of the second connector 321 (as shown FIG. 17) is 0.1-0.3 mm.

Figure 18:
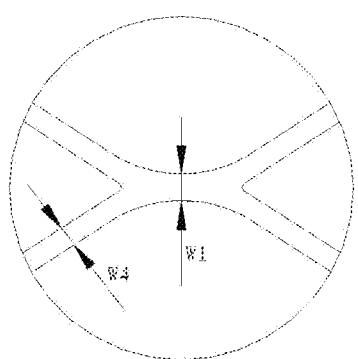
FIG. 18 is an enlarged diagram of the first connector in Embodiments 3 and 4.
Figure 19:
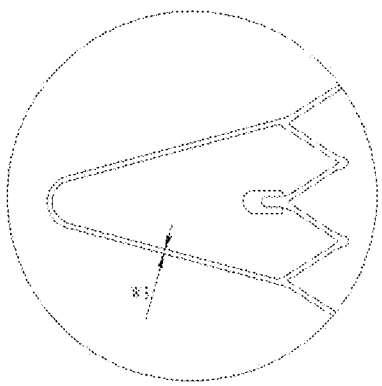
FIG. 19 is an enlarged diagram of the first repeating element in Embodiments 3 and 4.

The width W1 of the connector 221 (as shown FIG. 18) and the width W3 of the first repeating element 11 (as shown FIG. 19) are equal. The width W4 of the second repeating element 211 (as shown FIG. 18) and the width W5 of the third repeating element 311 (as shown FIG. 17) may employ a conventional width, for example, 0.1-0.3 mm.

In the present embodiment, the thickness of the intravascular stent is 0.1-0.3 mm (not shown), and the thickness of the intravascular stent refers to the difference between the external diameter and the inner diameter of the cross section of the intravascular stent.

In the present embodiment, the front end of the first repeating element 11 is a rounded corner, and the radius of the inner arc of the rounded corner is larger than 0.1 mm (not shown), so as to reduce the vascular stimulation from the intravascular stent.

In the present embodiment, the length L1 of the first repeating element 11 is 5-15 mm, preferably 10-15 mm, if the length of the first repeating element 11 is too long, it will cause the front ends of the first repeating element 11 contact the opposite vessel wall and cause harmful effects such as vascular stimulation; if the length of the first repeating element 11 is too short, it will affect the location of the intravascular stent in iliac vein, so as to cause the intravascular stent cannot be implanted in the desired position stably.

The length L2 of the central supporting segment 2 and the length L3 of the end supporting segment 3 are dependently 20-70 mm, preferably 30-60 mm, more preferably 30-40 mm, and the length L4 of the second repeating element 211 and the length L5 of the third repeating element 311 are dependently 1-7 mm, preferably 2-5 mm. That is, the central supporting segment 2 comprises substantially eight central supporting units 21, and the end supporting segment 3 comprises substantially eight end supporting units 21, of course, the number of the central supporting units 21 and the end supporting units 31 may be adjusted according to the actual requirement.

The total length L6 of intravascular stent in expanded state of the present invention is 50-120 mm, preferably 60-100 mm.

Figure 20:
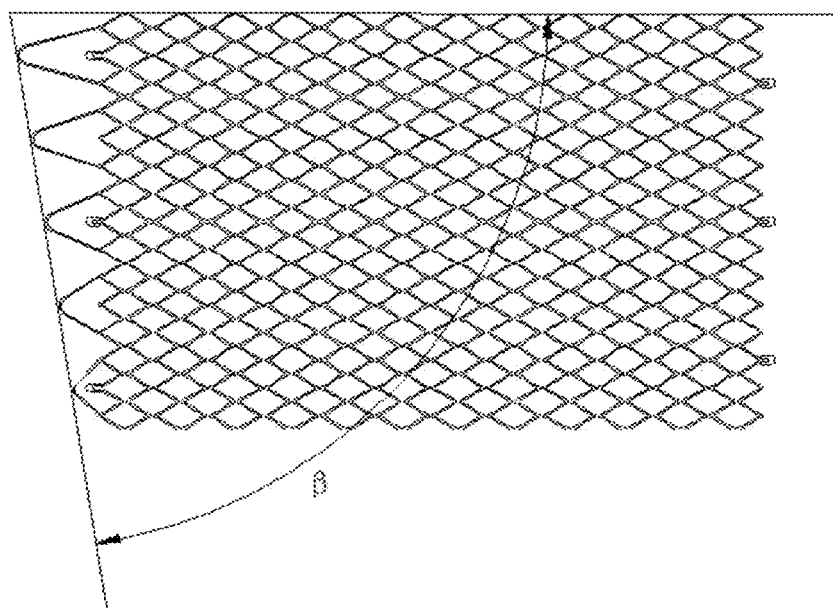
FIG. 20 is a schematic structure diagram of the intravascular stent of Embodiment 4 being unfolded to a plane.
Figure 21:
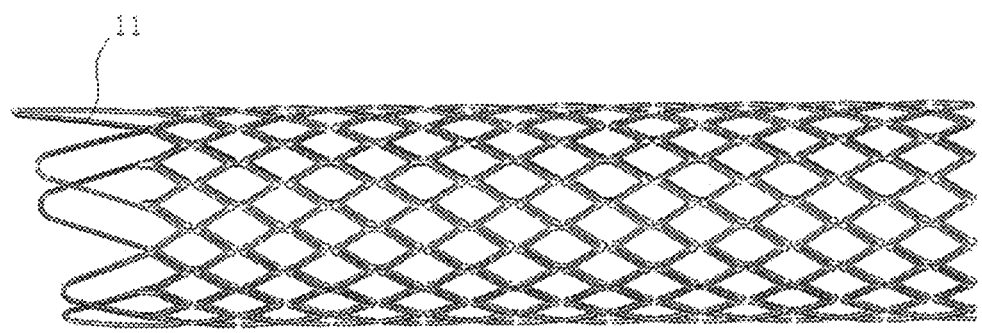
FIG. 21 is a space diagram of the intravascular stent of Embodiment 4 in the expanded state (the extending direction of the positioning segment is in accordance with the axial direction of the intravascular stent)
Figure 22:
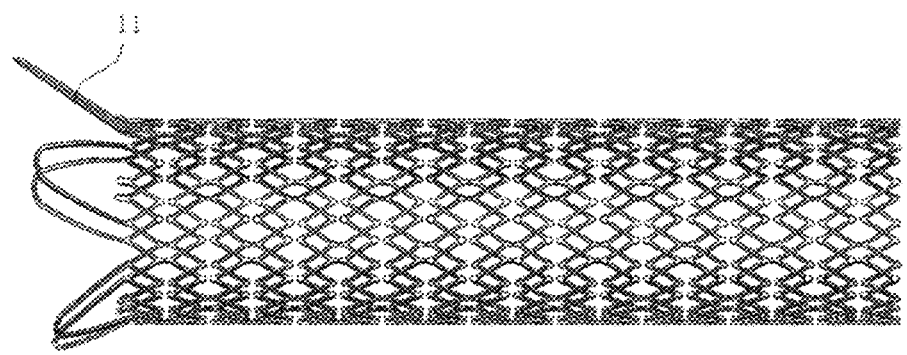
FIG. 22 is a space diagram of an intravascular stent of Embodiment 4 in the expanded state (the positioning segment is in a hydraucone shape)
Figures 23, 24:
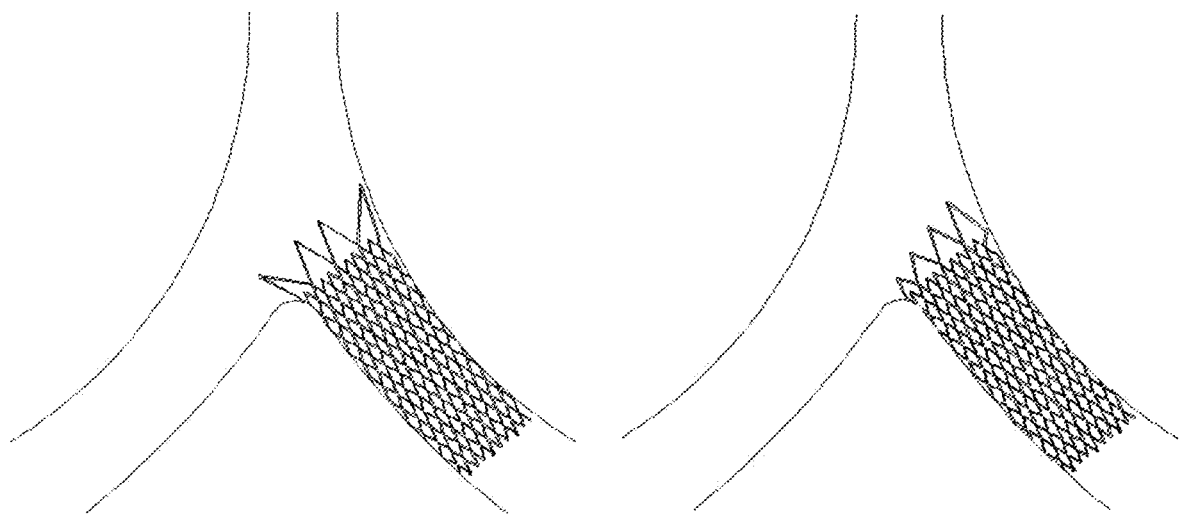
FIG. 23 is a schematic diagram of the intravascular stent of Embodiment 3 implanted in iliac vein (the positioning segment is in a hydraucone shape)
FIG. 24 is a schematic diagram of an intravascular stent of Embodiment 4 implanted in iliac vein (the extending direction of the positioning segment is in accordance with the axial direction of the intravascular stent)
Figures 25, 26:
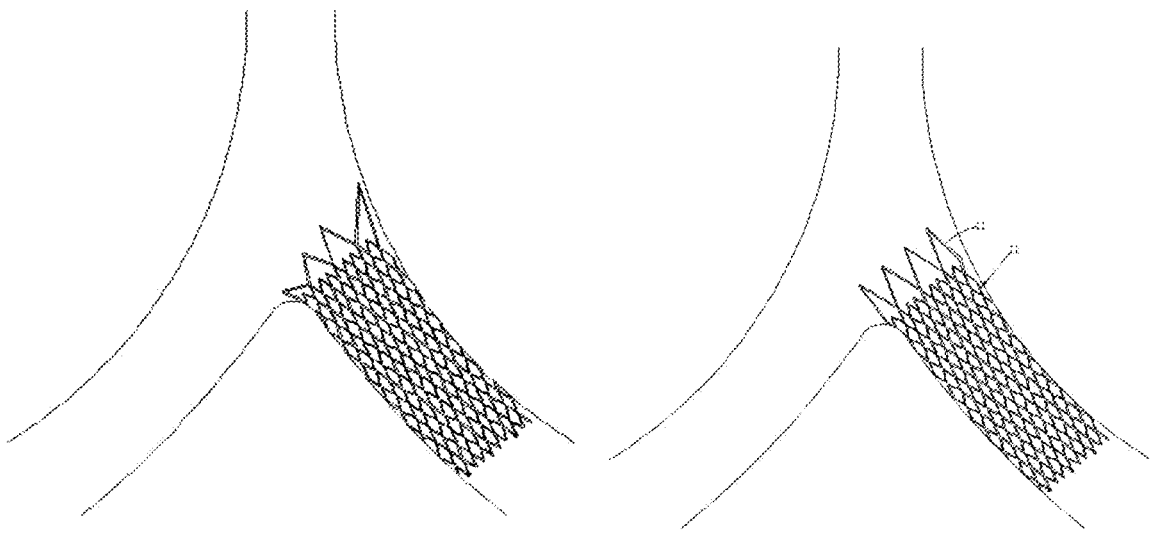
FIG. 25 is a schematic diagram of the intravascular stent of Embodiment 4 implanted in iliac vein (the positioning segment is in a hydraucone shape)
FIG. 26 is a schematic diagram of an intravascular stent of Embodiment 5 implanted in iliac vein (the extending direction of the positioning segment is in accordance with the axial direction of the intravascular stent)

The above mentioned contents of Embodiments 3 and 4 are the same, but differ in that: in Embodiment 3, the plane formed by the front ends of the plurality of the first repeating elements 11 is vertical to the axis of the intravascular stent, as shown in FIGS. 14 and 15. In Embodiment 4, the plane formed by the front ends of the plurality of the first repeating elements 11 intersects with the axis of the intravascular stent, and the angle β between the plane formed by the front ends of the plurality of the first repeating elements 11 and the axis of the intravascular stent is 45°-89°, as shown in FIGS. 20-22, wherein, in FIGS. 20-22, the angle β between the plane formed by the front ends of the plurality of the first repeating elements 11 and the axis of the intravascular stent is 70°, and in Embodiment 4, the lengths of the first repeating elements 11 vary gradually, however, the length range thereof should be in the above defined length range of the first repeating elements 11.

The above describes the present disclosure in detail, and is intended to make those skilled in the art being able to understand the present disclosure and thereby implement it, and should not be concluded to limit the protective scope of this disclosure. The present disclosure is not limit to the above embodiments. Any equivalent variations or modifications according to the spirit of the present disclosure should be covered by the protective scope of the present disclosure.

The invention claimed is:

1. An intravascular stent, capable of changing to an expanded state with an expanded second cross-sectional diameter from a compressed state with a first cross-sectional diameter, wherein,
the intravascular stent comprises a positioning segment and a supporting segment connected in an axial direction of the intravascular stent,
the positioning segment comprises a plurality of first repeating elements distributed in a circumferential direction along the intravascular stent,
the supporting segment comprises at least two supporting units and at least one connecting unit connected in the axial direction of the intravascular stent, the at least two supporting units each comprising a plurality of second repeating elements distributed in the circumferential direction along the intravascular stent,
the number of the first repeating elements differs from the number of the second repeating elements of each of the at least two supporting units, and holes formed by the first repeating elements are larger than holes formed by the second repeating elements in size so as to avoid the formation of thrombosis caused by a small hole of the intravascular stent or effect on the blood flow of an opposite iliac vein caused by the positioning segment, and the second repeating elements of the at least two supporting units located at a front end and a rear end of the supporting segment are one-to-one correspondingly connected with the second repeating elements of another adjacent supporting unit to form close-loop structures, the front end of the supporting segment is connected with a plurality of first developing units, the number of the first developing units being 3 to 10, a length of one of the first repeating elements is 5-15 mm, a length of the supporting segment is 40-140 mm, and a thickness of the intravascular stent is 0.1-0.3 mm;
the intravascular stent is configured to be used for an iliac vein stent.

2. The intravascular stent according to claim 1, wherein, the number of the first repeating elements is less than the number of the second repeating elements of each of the at least two supporting units.

3. The intravascular stent according to claim 1, wherein, the rear end of the supporting segment is connected with a plurality of second developing units, the number of the second developing units being 3 to 10.

4. The intravascular stent according to claim 1, wherein, a front end of the positioning segment is connected with a plurality of second developing units, the number of the third developing units being 3 to 10.

5. The intravascular stent according to claim 1, wherein, the at least one connecting unit comprises a plurality of connectors distributed in the circumferential direction along the intravascular stent, the number of the connectors being not more than the number of the second repeating elements.

6. The intravascular stent according to claim 5, wherein, a width of the plurality of connectors is 0.1 mm to 0.3 mm.

7. The intravascular stent according to claim 5, wherein, the number of the connectors of the connecting unit located at the front end and the rear end of the supporting segment is equal to the number of the second repeating elements of the supporting units located at the front end and the rear end of the supporting segment, and the number of the connectors of the connecting unit located in a middle portion of the supporting segment is less than the number of the second repeating elements of the supporting units located in the middle portion of the supporting segment.

8. The intravascular stent according to claim 5, wherein, the supporting segment comprises a first supporting part, a second supporting part and a third supporting part connected successively in the axial direction of the intravascular stent, each of the first supporting part, the second supporting part and the third supporting part comprises at least two supporting units and at least one connecting unit connected in the axial direction of the intravascular stent, and the positioning segment is connected with the first supporting part, the structure formed by two adjacent supporting units of the first supporting part is alternately arranged by closed-loop and open-loop in the axial direction.

9. The intravascular stent according to claim 8, wherein, the structure formed by two adjacent supporting units of the second supporting part is open-loop.

10. The intravascular stent according to claim 8, wherein, the length of the first supporting part accounts for 0.4-0.6 of the total length of the supporting segment.

11. The intravascular stent according to claim 1, wherein, an angle between a plane formed by front ends of the plurality of first repeating elements and an axis of the intravascular stent is 45°~90°.

12. The intravascular stent according to claim 1, wherein, the material of the intravascular stent is one or more selected from stainless steel, memory alloy, nickel-titanium alloy, titanium alloy, tantalum alloy, cobalt-chromium alloy, biodegradable metal, biodegradable polymer, magnesium alloy, pure iron.

13. The intravascular stent according to claim 1, wherein, an angle between an extending direction of the positioning segment and an axis of the intravascular stent is 0°~60°.

* * * * *